US005295487A

United States Patent [19]
Saitoh et al.

[11] Patent Number: 5,295,487

[45] Date of Patent: Mar. 22, 1994

[54] ULTRASONIC PROBE

[75] Inventors: Shiroh Saitoh, Yokohama; Mamoru Izumi, Tokyo; Senji Shimanuki, Atsugi; Shinichi Hashimoto, Kawasaki; Yohachi Yamashita, Yokohama, all of Japan

[73] Assignee: Kabushiki Kaisha Toshiba, Kawasaki, Japan

[21] Appl. No.: 15,425

[22] Filed: Feb. 9, 1993

[30] Foreign Application Priority Data

Feb. 12, 1992 [JP] Japan .................................... 4-25134
May 22, 1992 [JP] Japan .................................... 4-130303

[51] Int. Cl.[5] .................................... A61B 8/00
[52] U.S. Cl. .................................... 128/662.03; 310/334
[58] Field of Search .................................... 310/335-337, 310/358, 366, 368-369; 29/25.35; 128/660.07, 661.01, 662.03

[56] References Cited

U.S. PATENT DOCUMENTS 4,704,774 11/1987 Fujii et al. .................... 310/335 X

FOREIGN PATENT DOCUMENTS 0056375 4/1983 Japan .................................... 310/358

OTHER PUBLICATIONS

Takeuchi, H. et al "New Piezo-Ceramics with Zero Temp. Coeff. for Acoustic Wave Applns", Conf: 1980 UTS Symp. Bistib 5-7 Nov. 1980 pp. 400-409.

*Primary Examiner*—Francis Jaworski
*Attorney, Agent, or Firm*—Oblon, Spivak, McClelland, Maier & Neustadt

[57] ABSTRACT

An ultrasonic probe includes an ultrasonic transmitting-/receiving element which uses a piezoelectric member constituted by a solid-solution based single crystal of zinc lead niobate-lead titanate, so that low-frequency driving can be achieved, the thickness of the piezoelectric member in the direction of vibration can be decreased, matching with a transmitting/receiving circuit can be easily made, and the sensitivity can be improved. The ultrasonic probe includes an ultrasonic transmitting/receiving element having a piezoelectric member constituted by a solid-solution based single crystal of zinc lead niobate-lead titanate and a pair of electrodes formed on an ultrasonic transmitting/receiving surface of the piezoelectric member and a surface opposite to the transmitting/receiving surface, respectively.

19 Claims, 5 Drawing Sheets

ULTRASONIC PROBE

BACKGROUND OF THE INVENTION

1. Field of the Invention

The present invention relates to an ultrasonic probe and, more particularly, to an ultrasonic probe useful in a medical diagnosing apparatus.

2. Description of the Related Art

An ultrasonic probe has an ultrasonic transmitting/receiving element having a piezoelectric element. The ultrasonic probe is used for imaging the internal state of a target by radiating an ultrasonic wave toward the target and receiving an echo reflected by an interface having a different acoustic impedance of the target. An ultrasonic imaging apparatus incorporating such an ultrasonic probe is applied to, e.g., a medical diagnosing apparatus for inspecting the interior of a human body and an inspecting apparatus for inspecting the interior of a metal welding portion.

As an example of the medical diagnosing apparatus, in addition to the tomographic image (B mode image) display of the human body, there has been recently developed an apparatus employing the "Color Flow Mapping (CFM) method" capable of performing two-dimensional color display of the speed of the blood flow of, e.g., the heart, liver, and carotid artery, by utilizing a Doppler shift in ultrasonic wave caused by the blood flow. The diagnosing performance has been remarkably improved by this medical diagnosing apparatus. The medical diagnosing apparatus employing the CFM method is used for diagnosis of all the internal organs, e.g., the uterus, liver, and spleen, of the human body. Further studies are in progress aiming at an apparatus capable of diagnosing coronary thrombus.

In the case of the former B mode image, a high-resolution image must be obtained at a high sensitivity so that even a small change to a morbid state and a body cavity at a deep location caused by a change in body can be clearly seen. In the latter Doppler mode capable of obtaining a CFM image, since the echo reflected by a small blood cell having a diameter of about several fm is used, the obtained signal level is lower than that obtained in the B mode image, and thus a higher sensitivity is required.

Conventionally, ultrasonic transmitting/receiving elements having the structures as follows are used in terms of their performance:

(1) Ultrasonic attenuation caused by irradiating a living body with an ultrasonic wave by an ultrasonic probe is about 0.5 to 1 dB/MHz.cm except in bones. Thus, in order to obtain a high-sensitivity signal from the living body, it is preferable to decrease the frequency of the ultrasonic wave radiated by the ultrasonic transmitting/receiving element. When, however, the frequency is excessively decreased, the wavelength of the frequency is increased to sometimes degrade the resolution. Therefore, an ultrasonic wave having a frequency of 2 to 10 MHz is usually radiated.

(2) The piezoelectric member of the ultrasonic transmitting/receiving element must be constituted by a material having a large electromechanical coupling coefficient and a large dielectric constant so that loss caused by cables and the stray capacitance of the apparatus is small and that the piezoelectric member be easily matched with a transmitting/receiving circuit. For this reason, the piezoelectric member is mainly constituted by a titanate lead zirconate (PZT)-based ceramic.

(3) An array-type ultrasonic probe constituted by arranging several tens to about 200 ultrasonic transmitting/receiving elements each having a strip-shaped piezoelectric member has a high resolution.

However, the conventional ultrasonic probe has the following problems.

(a) The ultrasonic transmitting/receiving element usually radiates an ultrasonic wave by utilizing resonance of the vibration of the piezoelectric member in the direction of thickness. To decrease the influence of the attenuation in ultrasonic wave from a living body, the frequency of the ultrasonic wave must be decreased, as described above. To decrease the frequency of the wave, the piezoelectric member must be thicker. For example, in order to radiate an ultrasonic wave having a frequency of 2.5 MHz, the thickness of the piezoelectric member comprising the PZT-based ceramic must be set to 600 μm in the direction of vibration. When the thickness of the piezoelectric member is increased in this manner, various problems occur. More specifically, to form a strip-shaped piezoelectric member from a PZT-based ceramic block, a dicer used in dicing a semiconductor silicon wafer and the like is used. When the thickness of the piezoelectric member in the direction of vibration is increased, the depth of cut when dicing is performed at a predetermined pitch is increased. If, for this reason, dicing is performed by using a thin blade, the cutting groove becomes oblique, the cut portion winds, or the piezoelectric member can be damaged. If dicing is performed by using a thick plate in order to avoid them, the cutting amount is increased. Then, since the size of the PZT-based ceramic blocks before dicing is predetermined, the area of the ultrasonic transmitting/receiving surface of each piezoelectric member is decreased. As a result, the sensitivity is decreased, and the side lobe (grating lobe) level is increased.

(b) When the array-type ultrasonic probe is brought into contact with the living body, since the diameter of the ultrasonic wave radiating surface cannot be increased, as the number of ultrasonic transmitting/receiving elements is increased, the impedance per piezoelectric member is increased, and matching with the transmitting/receiving circuit becomes difficult to obtain. Regarding matching, poor matching can be avoided by using the PZT-based ceramic having a large relative dielectric constant as the piezoelectric member. However, since the electromechanical coupling coefficient of the PZT-based ceramic is decreased when the relative dielectric constant exceeds 3,000, the sensitivity is decreased, thus causing another problem.

Regarding the problem (b) described above, matching with the transmitting/receiving circuit is obtained by forming the piezoelectric member as a multilayered structure or by incorporating an impedance converter. However, in a multilayered structure, although the transmitting sensitivity is increased in accordance with the number of layers, the receiving sensitivity is inversely proportional to the number of layers. Therefore, the application of the multilayered piezoelectric member is limited to special cases, e.g., a case wherein the piezoelectric member is smaller than usual and a case wherein the cable is long. When an impedance converter such as an emitter-follower is used, the size of the ultrasonic probe is increased, and the frequency band is narrowed due to the frequency characteristics inherent to the impedance converter.

It is known that a piezoelectric member constituted by a polymeric material, e.g., lead metaniobate, polyvinylidene fluoride, or a copolymer thereof, has a small frequency constant and that its thickness ca be smaller than that constituted by a PZT-based ceramic even if it has a low frequency. However, the polymeric material has a small dielectric constant and a small electromechanical coupling coefficient and is not thus practical.

As described above, when a high-sensitivity low-frequency driving ultrasonic probe which causes small attenuation in ultrasonic wave in a living body is to be obtained, if a conventional PZT-based ceramic is used, the thickness of the probe becomes large. For this reason, if a thin blade is used to perform dicing to obtain strip-shaped piezoelectric members, the cutting groove becomes oblique, the cut portion winds, or the piezoelectric member can be damaged. If dicing is performed by using a thick plate, as the cutting portion is increased, the area of the ultrasonic wave transmitting/receiving surface of each piezoelectric member is decreased. Then, the sensitivity is decreased, and the side lobe level is increased. Furthermore, when the thickness of the piezoelectric member is increased, the electric impedance is increased, and matching with the transmitting/receiving circuit becomes difficult to obtain.

SUMMARY OF THE INVENTION

It is an object of the present invention to provide an ultrasonic probe having an ultrasonic transmitting/receiving element which achieves low-frequency driving, in which the thickness of the piezoelectric member in the direction of vibration can be decreased, which can easily obtain matching with a transmitting/receiving circuit, and which increases the sensitivity.

It is another object of the present invention to provide an array-type ultrasonic probe in which the frequency of the ultrasonic wave transmitted from the ultrasonic transmitting/receiving surface of each ultrasonic transmitting/receiving element can be set constant and which can obtain a high-resolution ultrasonic beam.

According to the present invention, there is provided an ultrasonic probe comprising an ultrasonic transmitting/receiving element having a piezoelectric member constituted by a solid-solution based single crystal of zinc lead niobate-lead titanate and a pair of electrodes respectively formed on an ultrasonic transmitting/receiving surface of the piezoelectric member and a surface opposite to the transmitting/receiving surface.

According to the present invention, there is also provided an array-type ultrasonic probe in which a plurality of ultrasonic transmitting/receiving elements each having a piezoelectric member constituted by a single crystal and a pair of electrodes respectively formed on an ultrasonic transmitting/receiving surface of the piezoelectric member and a surface opposite to the transmitting/receiving surface are arranged, wherein the piezoelectric member has a predetermined uniform thickness, and has the ultrasonic transmitting/receiving surface curved in a recessed manner and extending at right angles to a direction along which the piezoelectric member is arranged, and the recessed ultrasonic transmitting/receiving surface having a central portion with a maximum electromechanical coupling coefficient.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description give above and the detailed description of the preferred embodiments given below, serve to explain the principles of the invention.

DESCRIPTION OF THE PREFERRED EMBODIMENTS

Figure 1:
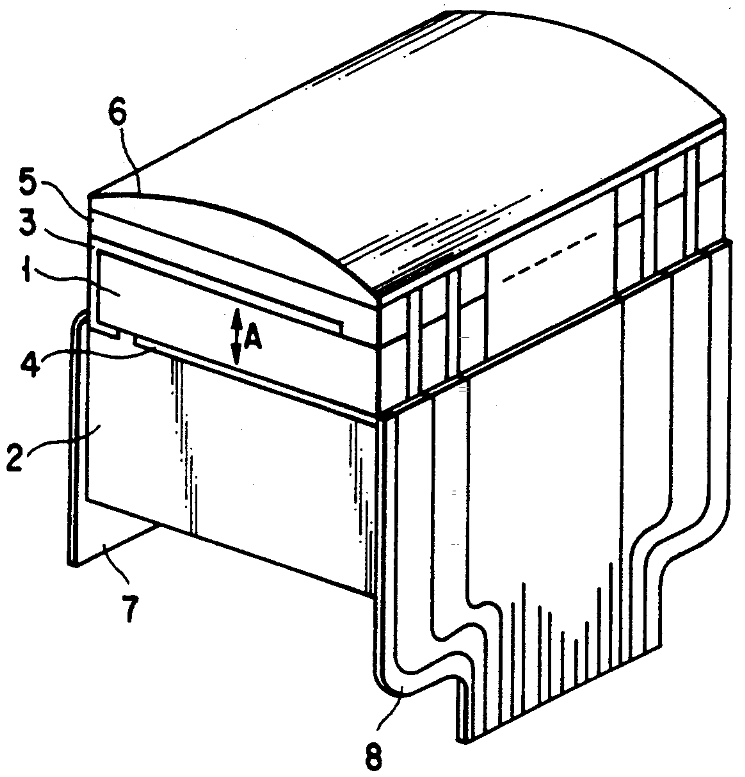
FIG. 1 is a perspective view showing an ultrasonic probe according to a embodiment of the present invention.

An ultrasonic probe according to an embodiment of the present invention will now be described in detail with reference to FIG. 1.

A plurality of piezoelectric members 1 constituted by a single crystal are bonded on a backing member 2 to be separated from each other. The piezoelectric members 1 vibrate in a direction of an arrow A in FIG. 1. A first electrode 3 is formed to extend from the ultrasonic transmitting/receiving surface of each piezoelectric member 1 to cover its side surface and part of its surface opposite to the transmitting/receiving surface. A second electrode 4 is formed on the other surface of each piezoelectric member 1 opposite to its transmitting/receiving surface to be spaced apart from the corresponding first electrode 3 at a desired distance. Each piezoelectric member 1 and the corresponding first and second electrodes 3 and 4 constitute an ultrasonic transmitting/receiving element. Acoustic matching layers 5 are formed on the ultrasonic transmitting/receiving surfaces of the piezoelectric members 1 including the respective first electrodes 3. An acoustic lens 6 is formed to cover the entire portions of the acoustic matching layers 5. A ground electrode plate 7 is connected to the first electrodes 3 by, e.g., soldering. A flexible printed wiring board 8 having a plurality of conductors (cables) is connected to the second electrodes 4, by, e.g., soldering.

The ultrasonic probe having the structure as shown in FIG. 1 is manufactured in accordance with, e.g., the following method.

Conductive films are deposited on the two surfaces of a single-crystal piece block by sputtering, and selective etching is performed to leave conductive films on the ultrasonic transmitting/receiving surface and the surface opposite to the transmitting/receiving surface of the single-crystal piece. The ground electrode plate 7 is bonded, by soldering, on the end portion of the conductive film located on the transmitting/receiving surface. An acoustic matching layer is formed on the conductive film located on a surface of the single-crystal piece serving as the ultrasonic transmitting/receiving surface. Subsequently, the flexible printed wiring board 8 having the plurality of conductors (cables) is bonded, by soldering, on the end portion of the conductive film located on the surface opposite to the transmitting/receiving surface, and the resultant structure is bonded on the backing member 2. By using a blade, dicing is performed from the acoustic matching layer to the conductive film located on the surface opposite to the transmitting/receiving surface of the single-crystal piece a plurality of times, thus forming the plurality of separated piezoelectric members 1 respectively having the first and second electrodes 3 and 4 on the backing member 2 and the plurality of acoustic matching layers 5 respectively arranged on the piezoelectric members 1. The acoustic lens 6 is formed on the acoustic matching layers 5, thus manufacturing an ultrasonic probe.

The piezoelectric members 1 are constituted by a solid-solution based single crystal of zinc lead niobate-lead titanate. Such a single crystal is fabricated in accordance with, e.g., the following method.

PbO, ZnO, $Nb_2O_5$, and $TiO_2$ each having a high chemical purity are used as the starting materials. The starting materials are purity-corrected, weighed such that zinc niobate (PZN) and lead titanate (PT) satisfy a desired molar ratio, and the same amount of PbO is added to the resultant powder as the flux. Distilled water is added to the resultant powder and mixed for a desired period of time in, e.g., a ball mill containing $ZrO_2$ balls. Water is removed from the obtained mixture. The mixture is sufficiently pulverized by a grinder, e.g., a Raika machine is placed in a rubber mold container and is rubber-pressed at a desired pressure. A solid material removed from the rubber mold is placed in, e.g., a platinum container having a desired volume and melted at a desired temperature. After cooling, the solid material is placed in the platinum container again and sealed with, e.g., a platinum lid, and the container is placed at the center of an electric furnace. The material is heated to a temperature higher than the melting temperature and is then slowly cooled to near the melting temperature at a desired temperature drop rate, and then the container is cooled down to room temperature. Then, nitric acid having a desired concentration is added in the container, the content in the container is boiled, and the fabricated solid-solution based single crystal is removed from the container.

The solid-solution based single crystal of zinc lead niobate-lead titanate can similarly be fabricated in accordance with, e.g., the Bridgman method, the Kyropoulous method, and the hydrothermal method, in addition to the flux method described above.

It is preferable to use a solid-solution based single crystal of zinc lead niobate-lead titanate whose molar fraction of lead titanate is 20% or less. When a piezoelectric member constituted by such a solid-solution based single crystal is used, the sound velocity can be decreased by 20% or more than that of a piezoelectric member constituted by the PZT ceramic, and thus an ultrasonic probe having a high sensitivity can be obtained.

It is more preferable to use a solid-solution based single crystal of zinc lead niobate-lead titanate having a composition expressed by the following formula:

$$Pb_A[(Zn_{1/3}Nb_{2/3})_{1-x}Ti_x)]_BO_3$$

(wherein x is defined $0.05 \leqq X \leqq 0.20$, and the stoichiometric ratio A/B is defined $0.98 \leqq A/B < 1.00$)

X in the formula is defined in the above manner due to the following reason. When x is set to be less than 0.05, the Curie temperature of the solid-solution based single crystal becomes low, and depolarization may undesirably occur during soldering of the flexible printed wiring board 7 or the ground electrode plate 8 or dicing of the solid-solution based single crystal. On the other hand, when x exceeds 0.20, a large electromechanical coupling coefficient cannot be obtained, and the dielectric constant is decreased, so that matching of the acoustic impedance of the transmitting/receiving circuit portion becomes difficult to obtain. Most preferably, x is 0.06 to 0.12.

When A/B of the above formula falls outside the above range, the reliability of the obtained ultrasonic probe in the actual operation may undesirably be degraded.

It is preferable that each piezoelectric member 1 has a thickness of 200 to 400 μm in the direction of vibration.

It is preferable that the ultrasonic transmitting/ receiving surface of each piezoelectric member 1 and a surface thereof opposite to the transmitting/receiving surface have an average surface roughness of 0.4 μm or less and a maximum surface roughness of 4 μm or less. When the average surface roughness and the maximum surface roughness exceed 0.4 μm and 4 μm, respectively, a long-term reliability, e.g., sensitivity may be degraded. Preferably, the average surface roughness and the maximum surface roughness are 0.3 μm or less and 3 μm or less, respectively.

It is preferable that each piezoelectric member 1 has an ultrasonic transmitting/receiving surface on the (001) plane. Such a piezoelectric member 1 can be fabricated by dicing the above-described solid-solution based single crystal in the vertical direction with respect to the [001] axis (C axis).

Each of the first and second electrodes 3 and 4 is made of a two-layered conductive film constituted by, e.g., Ti/Au, Ni/Au, or Cr/Au.

The ultrasonic probe shown in FIG. 1 according to the present invention uses the solid-solution based single crystal of zinc lead niobate-lead titanate as the piezoelectric members 1. Therefore, when electrodes are formed on the piezoelectric members constituted by the solid-solution based single crystal, thus performing polarization, a relative dielectric constant of about 2,200 can be obtained. Also, the ultrasonic transmitting-/receiving elements can be fabricated by dicing the solid-solution based single crystal in the vertical direction with respect to, e.g., the [001] axis to form strip-shaped piezoelectric members each of which has the ultrasonic transmitting/receiving surface on the (001) plane where a maximum electromechanical coupling coefficient ($k_{33}'$) can be obtained, and forming the first and second electrodes 3 and 4 on the (001) planes of the piezoelectric members 1. Each of these ultrasonic transmitting/receiving elements radiates an ultrasonic wave having a sound velocity of 2,700 to 3,000 m/s (frequency constant is 1,350 to 1,500 Hz.m) from the ultrasonic transmitting/receiving surface of its piezoelectric member 1 having an orientation of the (001) plane. Therefore, such an ultrasonic transmitting/receiving element can delay the sound velocity by about 30% as compared with that (4,000 m/s) of a conventional ultrasonic transmitting/receiving element having a piezoelectric member constituted by the PZT-based ceramic. Especially, when a piezoelectric member constituted by a solid-solution based single crystal of zinc lead niobate-lead titanate whose molar ratio of titanate as a component to increase the sound velocity is set to 20% or less is used, the sound velocity can be further decreased.

Assuming that the frequency of the ultrasonic wave radiated from the ultrasonic transmitting/receiving element is defined as $f_0$, that the sound velocity of the ultrasonic wave is v and that the thickness of the piezoelectric member of the element in the direction of vibration is t, $f_0$ can be expressed by the following equation:

$$f_0 = v/2t$$

Therefore, since the ultrasonic transmitting/receiving element can radiate an ultrasonic wave having a low sound velocity, even if the frequency ($f_0$) is set to a frequency lower than that defined in this equation, the thickness of the piezoelectric member of the element can be decreased. In other words, low-frequency driving capable of obtaining a high-sensitivity signal can be performed, and the thickness of the piezoelectric member constituted by the solid-solution based single crystal in the direction of vibration can be decreased.

From the above description, when the solid-solution based single crystal is to be formed into strips, the depth of cut of the blade of the dicing machine can be decreased, and cutting can be straightly performed without causing winding of the cutting portion even when a thin blade is used. In addition, the manufacture yield can be increased, and the ultrasonic transmitting-/receiving surface of the piezoelectric member can be maintained at a desired area, so that a high-performance ultrasonic probe having a decreased side lobe can be obtained.

The piezoelectric member constituted by the solid-solution based single crystal has a relative dielectric constant equal to or larger than that of the conventional piezoelectric member constituted by the PZT-based ceramic, as described above. Therefore, matching with the transmitting/receiving circuit can be easily obtained. As a result, a loss caused by a cable or the stray capacitance of the apparatus can be decreased, thus obtaining a high-sensitivity signal.

Furthermore, the ultrasonic transmitting/receiving element is formed by using a solid-solution based single crystal of zinc lead niobate-lead titanate having a composition expressed, by $Pb_A[(Zn_{1/3}Nb_{2/3})_{1-x}Ti_x)]_BO_3$ (wherein x is defined by the relationship: $0.05 \leq x \leq 0.20$, and the stoichiometric ratio A/B is defined by the relationship $0.98 \leq A/B < 1.00$), dicing the solid-solution based single crystal in the vertical direction with respect to, e.g., the [001] axis to form a strip having an ultrasonic transmitting/receiving surface on the (001) plane where the maximum electromechanical coupling coefficient ($k_{33}'$) can be obtained, and forming an electrode on each (001) plane. In such an ultrasonic transmitting/receiving element, the sound velocity of the ultrasonic wave radiated from the ultrasonic transmitting/receiving surface having the orientation of the (001) plane is 2,700 to 3,000 m/s (the frequency constant is 1,350 to 1,500 Hz.m), and a large electromechanical coupling coefficient $k_{33}'$ of 80 to 85% can be obtained. As a result, even when the ultrasonic probe having this ultrasonic transmitting/receiving element is connected to a diagnosing apparatus and a test is performed for about 1,000 hours at a pulse voltage of 50 to 150 V and a repetition frequency of 3 to 15 kHz, which are actual operation conditions, a high sensitivity obtained at the initial stage of operation can be maintained.

Furthermore, when the piezoelectric member constituting the ultrasonic transmitting/receiving element is constituted by the solid-solution based single crystal having ultrasonic transmitting/receiving surface and a surface opposite to the transmitting/receiving surface both having an average surface roughness of 0.4 μm or less and a maximum surface roughness of 4 μm or less, even when an actual operation test is performed for 1,000 hours or more at a pulse voltage of 50 to 150 V and a repetition frequency of 3 to 15 kHz, which are actual operation conditions, the sensitivity is not decreased, thus realizing an ultrasonic probe having an excellent long-term reliability.

Furthermore, in an ultrasonic transducer such as an ultrasonic generating element in which electrodes are formed on the ultrasonic generating surface of a piezoelectric member constituted by the solid-solution based single crystal of zinc lead niobate-lead titanate represented by the formula and a surface opposite to it, since a large electric field can be applied to the piezoelectric member constituted by the solid-solution based single crystal, the radiation sound wave can be increased. As a result, the ultrasonic generating element can be applied to the shock wave source of a stone destroying apparatus or thermotherapeutic apparatus which performs treatment by externally radiating the shock wave to a human body to finely destroy a liverstone or gallstone and naturally discharging the fragments of the destroyed stone. That is, the element can be applied to the transmitter of an ultrasonic therapeutic apparatus.

The piezoelectric member constituted by the solid-solution based single crystal has a specific weight of 8.2 to 8.5, which is close to that (7.5 to 8.0) of a conventional piezoelectric member constituted by the PZT-based ceramic and can be made thinner than the conventional piezoelectric member. Therefore, the overall weight can be decreased by about 25%. As a result, a lightweight stone destroying apparatus can be realized by assembling the ultrasonic generating element having the piezoelectric member to the transmitter. Since the transmitter of such a stone destroying apparatus can be finely aligned with the position of the stone with a good controllability, the stone destroying efficiency can be improved, and the size of the driving mechanism can be decreased.

Note that the electrodes 3 and 4 need not be arranged or the flexible printed wiring board 7 and the ground electrode plate 8 need not be connected to the electrodes 3 and 4 as shown in FIG. 1. For example, the flexible printed wiring board 7 and the ground electrode plate 8 may be connected to the electrodes 3 and 4 by using a conductive paste or in accordance with resistance welding, in addition to soldering.

FIG. 1 shows an array-type ultrasonic probe. However, the present invention also incorporates an ultrasonic probe having a single ultrasonic transmitting/receiving element.

An array-type ultrasonic probe according to another embodiment of the present invention will now be described in detail with reference to FIG. 2.

A plurality of piezoelectric members 11 constituted by a single crystal are bonded on a backing member 12 so as to be separated from each other. The piezoelectric members 11 have a predetermined uniform thickness, and have ultrasonic transmitting/receiving surfaces curved in the recessed manner and extending at right angles to a direction along which they are arranged. The central portion of each recessed ultrasonic transmitting/ receiving surface has a maximum electromechanical coupling coefficient. The piezoelectric members 11 vibrate in the direction of arrow A in FIG. 2. A first electrode 13 is formed on the recessed ultrasonic transmitting/ receiving surface of each piezoelectric member 11. A second electrode 14 is positioned between the projecting surface of each piezoelectric member 11 opposite to the transmitting/receiving surface and the backing member 12, and is in good contact with the corresponding piezoelectric member 11. Each piezoelectric member 11 and the corresponding first and second electrodes 13 and 14 constitute an ultrasonic transmitting/receiving element. Acoustic matching layers 15 are formed on the corresponding first electrodes 13. The acoustic matching layers 15 have a predetermined uniform thickness, and have surfaces curved in the recessed manner and extending at right angles to a direction along which they are arranged. A ground electrode plate 16 is positioned between the first electrodes 13 and the acoustic matching layers 15 in a direction along which the piezoelectric members 11 are arranged, and connected to the first electrodes 13. A flexible printed wiring board 17 having a plurality of conductors (cables) is located between the second electrodes 14 and the backing member 12 in the direction along which the piezoelectric members 11 are aligned, and connected to the second electrodes 14.

Figure 2:
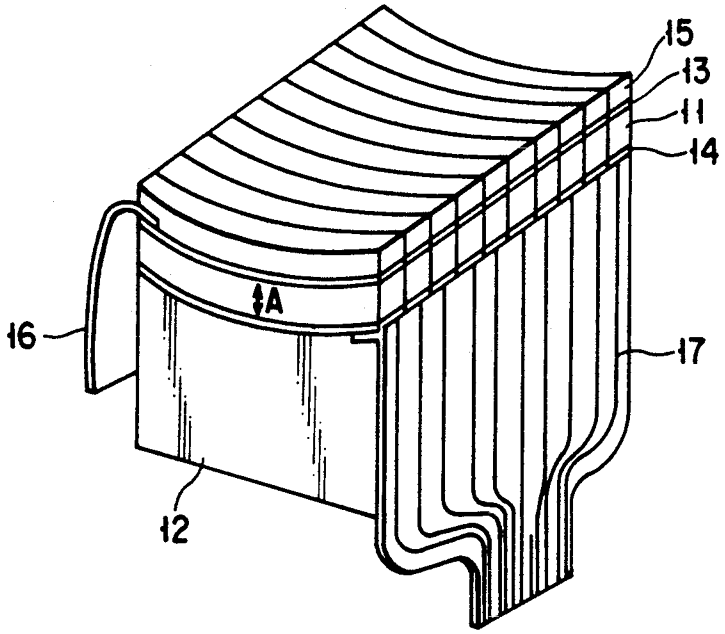
FIG. 2 is a perspective view showing an ultrasonic probe according to another embodiment of the present invention.

The array-type ultrasonic probe having the structure as shown in FIG. 2 is manufactured in accordance with, e.g., the following method.

A single-crystal piece block having a predetermined uniform thickness, and having an ultrasonic transmitting/receiving surface curved in the recessed manner, a surface opposite to transmitting/receiving surface curved in the projecting manner is formed. Conductive films are deposited on the two surfaces of the single-crystal piece by sputtering. The ground electrode plate 16 is bonded, by using a conductive paste, on the end portion of the conductive film located on the recessed surface of the piezoelectric member in a direction perpendicular to a direction along which the single-crystal piece is curved. An acoustic matching layer having a predetermined uniform thickness and a recessed curved surface, in the same manner as the single-crystal piece, is formed on the conductive film located on the recessed surface of the piezoelectric member including the ground electrode plate 16. Subsequently, the flexible printed wiring board 17 having the plurality of conductors (cables) is bonded, by using a conductive paste, on the end portion of the conductive film located on the projecting surface of the single-crystal piece in a direction perpendicular to the curved direction of the single-crystal piece, and the resultant structure is bonded on the backing member 12. Then, by using a blade, dicing is performed from the acoustic matching layer to the conductive film located on the projecting surface of the single-crystal piece a plurality of times in a direction parallel to the curved direction of the piezoelectric member, thus manufacturing the array-type ultrasonic probe in which each of the plurality of separated piezoelectric members 11 is formed to have the first and second electrodes 13 and 14 on the backing member 12, and the plurality of acoustic matching layers 15 are respectively arranged on the piezoelectric members 11.

The piezoelectric members 11 are constituted by, e.g., a solid-solution based single crystal of zinc lead niobate-lead titanate. It is preferable to use a solid-solution based single crystal of zinc lead niobate-lead titanate whose molar fraction of lead titanate is 20% or less. It is more preferable to use a solid-solution based single crystal of zinc lead niobate-lead titanate having a composition expressed by a formula: $Pb_A[(Zn_{1/3}Nb_{2/3})_{1-x}Ti_x)]_BO_3$ (wherein x is defined $0.05 \leqq x \leqq 0.20$, and the stoichiometric ratio A/B is defined $0.98 \leqq A/B < 1.00$).

In order to set the central portions of the recessed ultrasonic transmitting/receiving surfaces of the piezoelectric members 11 so as to have the maximum electromechanical coupling coefficients, for example, the crystal orientations of the central portions of the recessed ultrasonic transmitting/receiving surfaces may be set such that their electromechanical coupling coefficients become the maximum. More particularly, when the piezoelectric members are constituted by a solid-solution based single crystal of zinc lead niobate-lead titanate, the crystal orientations of the central portions of their recessed ultrasonic transmitting/receiving surfaces are set in the (100) plane, so that the maximum electromechanical coupling coefficients can be obtained at their central portions.

It is preferable that each piezoelectric member 11 has a thickness of 200 to 400 μm in the direction of vibration.

It is preferable that the ultrasonic transmitting/receiving surface of each piezoelectric member 11 and a projecting surface thereof opposite to the transmitting/receiving surface have an average surface roughness of 0.4 μm or less and a maximum surface roughness of 4 μm or less. When the average surface roughness and the maximum surface roughness exceed 0.4 μm and 4 μm, respectively, a long range reliability, e.g., sensitivity may be degraded. Preferably, the average surface roughness and the maximum surface roughness are 0.3 μm or less and 3 μm or less, respectively.

Each of the first and second electrodes 13 and 14 is made of a two-layered conductive film constituted by, e.g., Ti/Au, Ni/Au, or Cr/Au.

In the array-type ultrasonic probe shown in FIG. 2 according to the present invention, a plurality of ultrasonic transmitting/receiving elements having the piezoelectric members 11 constituted by the single crystal are arranged. The piezoelectric members 11 have a predetermined uniform thickness, and have the ultrasonic transmitting/receiving surfaces curved in the recess manner in the direction along which they are arranged. The central portions of the recessed ultrasonic transmitting/receiving surfaces have the maximum electromechanical coupling coefficients. Therefore, these ultrasonic transmitting/receiving elements can decrease their electromechanical coupling coefficients toward the end portions of the recessed ultrasonic transmitting-/receiving surfaces of the piezoelectric members 11. As a result, the frequency of the ultrasonic wave radiated from the ultrasonic transmitting/receiving surface of each ultrasonic transmitting/receiving element can be set constant, and the electromechanical coupling coefficients can have a certain distribution. Therefore, the side lobe can be suppressed, and a high-resolution sound wave beam can be obtained. Also, the array-type ultrasonic probe shown in FIG. 2 can focus the ultrasonic beam without using an acoustic lens, unlike in the ultrasonic probe of FIG. 1 described above. Hence, an attenuation in ultrasonic wave caused depending on the position of the acoustic lens can be avoided, and the S/N ratio can be remarkably increased.

The preferred examples of the present invention will now be described in detail.

Example 1

PbO, ZnO, $Nb_2O_5$, and $TiO_2$ each having a high chemical purity were used as the starting materials. The starting materials were purity-corrected, weighed such that zinc niobate (PZN) and lead titanate (PT) satisfied a molar ratio of 91:9, and the same amount of PbO was added to the resultant powder as the flux. Distilled water was added to the resultant powder and mixed for 1 hour in a ball mill containing $ZrO_2$ balls. Water was removed from the obtained mixture. The mixture was sufficiently pulverized by a Raika machine, was placed in a rubber mold container, and was rubber-pressed at a pressure of 2 t/cm$^2$. 600 g of a solid material removed from the rubber mold were placed in a platinum container having a diameter of 50 mm and a volume of 250 cc and melted by increasing the temperature up to 900° C. within 4 hours. After cooling, 400 g of the solid material were placed in the platinum container again and sealed with a platinum lid, and the container was placed at the center of an electric furnace. The temperature was increased up to 1,250° C. within 5 hours and then slowly decreased down to 800° C. at a rate of 0.8° C./hr, and then the container was cooled down to room temperature. Then, nitric acid having a concentration of 20% was added in the platinum container, the content in the container was boiled for 8 hours, and the fabricated solid-solution based single crystal was removed from the container.

The single crystal obtained in accordance with this flux method had a non-fixed shape and a size of about 7 mm square. When part of the single crystal was pulverized and subjected to X-ray diffraction, it was confirmed to have a good crystal structure. When the pulverized powder was subjected to chemical analysis in accordance with inductively coupled plasm spectrometry (ICP), it was confirmed to have a composition of 91PZN-9PT in which zinc niobate (PZN) and lead titanate (PT) had a molar ratio of 91:9.

The [001]-axis orientation of the single crystal was obtained by using a Laue camera, and the single crystal was diced by a cutter in a direction perpendicular to this axis. Subsequently, Ni/Au electrodes were formed on the surfaces of the (001) plane of the diced single-crystal piece by sputtering. An electric field of 1 kV/mm was applied to the single-crystal piece in a silicone oil of 150° to 200° C. for 30 minutes, and the single-crystal piece was cooled while applying the electric field. This single-crystal piece, together with its electrodes, was diced into strips, and the capacitance, the resonance frequency, and the anti-resonance frequency of the strips were measured. As a result, it was confirmed that the relative dielectric constant was 2,200, the sound velocity was 2,850 m/s, and the electromechanical coupling coefficient $k_{33}'$ was 80 to 85%.

Furthermore, an array-type ultrasonic probe having the same structure as that shown in FIG. 1 was manufactured by using the single crystal of 91PZN-9PT described above. More specifically, a single-crystal piece having a thickness of 400 μm was formed from the single crystal of 91PZN-9PT. Ti/Au conductive film was deposited on the two surfaces of the (001) plane of this single-crystal piece block and two side surfaces of the piece block by sputtering, and selective etching was performed to remove part of the conductive film located on one side surface of the piezoelectric member and part of the conductive film located on a surface thereof opposite to the transmitting/receiving surface. A ground electrode plate 7 was bonded, by soldering, on the end portion of the conductive film located on the transmitting/receiving surface. An acoustic matching layer was formed on the conductive film located on a surface of the single-crystal piece, serving as the ultrasonic transmitting/receiving surface. Subsequently, a flexible printed wiring board 8 was bonded, by soldering, on the end portion of the conductive film located on the surface opposite to the transmitting/receiving surface, and the resultant structure was bonded on a backing member 2. Then, by using a blade having a thickness of 30 μm, dicing was performed from the acoustic matching layer to the conductive film located on the surface opposite to the transmitting/receiving surface of the single-crystal piece at a depth of cut of 1 mm and a pitch of 0.19 mm, thus forming strips. By this dicing, a plurality of separated piezoelectric members 1 each having first and second electrodes 3 and 4 on the backing member 2 and having a plurality of acoustic matching layers 5 respectively arranged on the piezoelectric members 1 were formed. When the cutting portion after dicing was observed with a microscope from its upper and side portions, no winding cutting portion or inclined cutting portion was found. An acoustic lens 6 was formed on the acoustic matching layers 5, a plurality of cables each having an electrostatic capacity of 110 pF/m and a length of 2 m were connected to the flexible printed wiring board 8, thus manufacturing an array-type ultrasonic probe.

The reflected echo of the ultrasonic probe was measured in accordance with the pulse echo method. All the ultrasonic transmitting/receiving elements radiated echoes each having a center frequency of about 2.5 MHz.

Comparative Example

An ultrasonic probe similar to that obtained in Example 1 was manufactured by using a piezoelectric member constituted by a PZT-based ceramic having a relative dielectric constant of 2,000. At this time, in order to manufacture an ultrasonic probe that radiates an echo having a center frequency of about 2.5 MHz, the PZT-based ceramic block used as the piezoelectric member must have a thickness of 600 $\mu$m. Accordingly, when this ceramic block is to be diced by using a blade, the depth of cut must be set to about 1.3 mm. When dicing was performed by using a blade having a thickness of 30 $\mu$m from the acoustic matching layer to the conductive film located on the surface opposite to the transmitting-/receiving surface of the ceramic block to form strips, the blade cut into the single-crystal piece obliquely. As a result, when the impedance characteristics of the ultrasonic transmitting/receiving elements after dicing were measured, 5% of the elements were defective.

Therefore, the blade was exchanged for a blade having a thickness of 50 $\mu$m. Dicing was performed in the same manner, an array-shaped ultrasonic probe having a structure similar to that shown in FIG. 1 was manufactured, and the pulse echo was measured. As a result, the echo sensitivity was degraded by about 3 dB from that obtained in Example 1.

The sound field of the ultrasonic probes of Example 1 and the Comparative Example were measured. The side lobe level was measured in a state wherein the beam was deflected by 60° by controlling the delay time of the pulse to be applied. As a result, the ultrasonic probe of Example 1 had a side lobe level lower than that of the ultrasonic probe of the Comparative Example by about 10 dB.

The sound velocities of the longitudinal waves of the ultrasonic probes of Example 1 and the Comparative Example were measured. As a result, the ultrasonic probe of Example 1 had a sound velocity of 2,800 m/s, which was lower than the sound velocity of 4,000 m/s of the ultrasonic probe of the Comparative Example by about 30%.

Examples 2–4, Reference Examples 1–3

PbO, ZnO, $Nb_2O_5$, and $TiO_2$ each having a high chemical purity were used as the starting materials. The starting materials were purity-corrected, weighed in predetermined amounts, and the same amount of PbO was added to the resultant powder as the flux. Alcohol was added to the resultant powder and mixed for 1 hour in a ball mill containing $ZrO_2$ balls. Alcohol was removed from the obtained mixture. The mixture was sufficiently pulverized by a Raika machine, was placed in a rubber mold container, and was rubber-pressed at a pressure of 2 t/cm$^2$. 1,000 g of a solid material removed from the rubber mold were placed in a platinum container having a diameter of 50 mm and a volume of 250 cc and sealed with a platinum lid, and the container was placed at the center of an electric furnace. The temperature was increased up to 1,000° to 1,300° C. within 5 hours and was then slowly decreased down to 700° to 900° C, at a rate of 0.5° C./hr to 5° C./hr. In this slow cooling, air was blown to the lower portion of the container at a flow rate of 10 to 1,000 ml/min to selectively cool the lower portion of the container, and thereafter the container was cooled down to room temperature. Then, nitric acid having a concentration of 50% was added in the platinum container, the content in the container was boiled for 8 hours to melt the flux portion, and the fabricated solid-solution based single crystal was removed from the container.

In the fabrication of the single crystal, six types of single crystals each having a color of pale yellow to dark brown and a perovskite structure were obtained by controlling the amount of flux, the maximum temperature, and the cooling rate. Each of the obtained single crystals had a non-fixed shape and a size of about 10 mm square. When part of each single crystal was pulverized and subjected to X-ray diffraction, it was confirmed to have a good crystal structure. The pulverized powder was subjected to chemical analysis in accordance with ICP. Table 1 below shows the obtained results. Note that Table 1 also includes the stoichiometric ratio A/B obtained when the composition of each single crystal was represented by a formula $Pb_A[(Zn_{1/3}Nb_{2/3})_{1-x}Ti_x)]_BO_3$.

TABLE 1

| | PbO (wt %) | ZnO (wt %) | $Nb_2O_5$ (wt %) | $TiO_2$ (wt %) | Stoichiometric Ratio A/B |
|---|---|---|---|---|---|
| Reference Example 1 | 66.82 | 7.82 | 23.78 | 2.12 | 1.015 |
| Reference Example 2 | 66.49 | 7.35 | 24.02 | 2.14 | 1.000 |
| Example 2 | 66.38 | 7.38 | 24.10 | 2.15 | 0.995 |
| Example 3 | 66.27 | 7.40 | 24.18 | 2.16 | 0.990 |
| Example 4 | 66.09 | 7.44 | 24.31 | 2.17 | 0.982 |
| Reference Example 3 | 65.81 | 7.50 | 24.51 | 2.19 | 0.970 |

The [001]-axis orientation of each single crystal was obtained by using a Laue camera, and the single crystal was diced by a cutter in a direction perpendicular to this axis. Subsequently, Ni/Au electrodes were formed on the surfaces of the (001) plane of the diced single-crystal piece by sputtering. An electric field of 1 kV/mm was applied to the single-crystal piece in a silicone oil of 150° to 200° C. for 30 minutes, and the single-crystal piece was cooled while applying the electric field. Each single-crystal piece, together with its electrodes, was diced into strips, and the capacitance, the resonance frequency, and the anti-resonance frequency of the strips were measured. As a result, it was confirmed that the relative dielectric constant was 2,000 to 2,800, the sound velocity was 2,700 to 3,000 m/s, and the electromechanical coupling coefficient $k_{33}'$ was 80 to 85%.

Furthermore, an array-type ultrasonic probe (having 96 elements) having the same structure as that shown in FIG. 1 was manufactured by using each single crystal, following the same procedures as in Example 1. The reflected echo of each obtained ultrasonic probe was measured in accordance with the pulse echo method. As a result, all the ultrasonic transmitting/receiving elements radiated echoes each having a center frequency of about 2.5 MHz.

The array-type ultrasonic probes of Examples 2 to 4 and Reference Examples 1 to 3 each having 96 elements were subjected to the actual operation test of about 1,000 hours with a rectangular double pulse having a repetition frequency of 5 kHz, a voltage of 100 V, a duty ratio of 1:1, and a pulse width of 0.2 $\mu$s. The peak value of the reflected echo was measured. The number of defective ones of the 96 elements incorporated in each probe was checked with a definition that an element whose peak value was degraded by 30 or more the value obtained before the actual operation test was a defective element. The following Table 2 shows the results.

TABLE 2

| | Stoichiometric Ratio A/B | Number of Defective Elements After Actual Operation Test |
|---|---|---|
| Example 2 | 0.995 | 0/96 |
| Example 3 | 0.990 | 0/96 |
| Example 4 | 0.982 | 0/96 |
| Reference Example 1 | 1.015 | 57/96 |
| Reference Example 2 | 1.000 | 22/96 |
| Reference Example 3 | 0.970 | 28/96 |

As is apparent from Table 2, the array-type ultrasonic probes of Examples 2 to 4 each using a piezoelectric member constituted by a single crystal having a stoichiometric ratio A/B satisfying the relationship $0.98 \leqq A/B < 1.00$ can maintain high reliability over a long period of time.

Ultrasonic probes having the same structures as that shown in FIG. 1 were manufactured by using piezoelectric members diced from single crystals obtained by changing the amount of lead titanate in the solid-solution based single crystal of zinc lead niobate-lead titanate in the range of 5 to 20 mol%. These ultrasonic probes had almost the same effects on the long-term reliability resulted from the stoichiometric ratio.

Example 5

Figure 3:
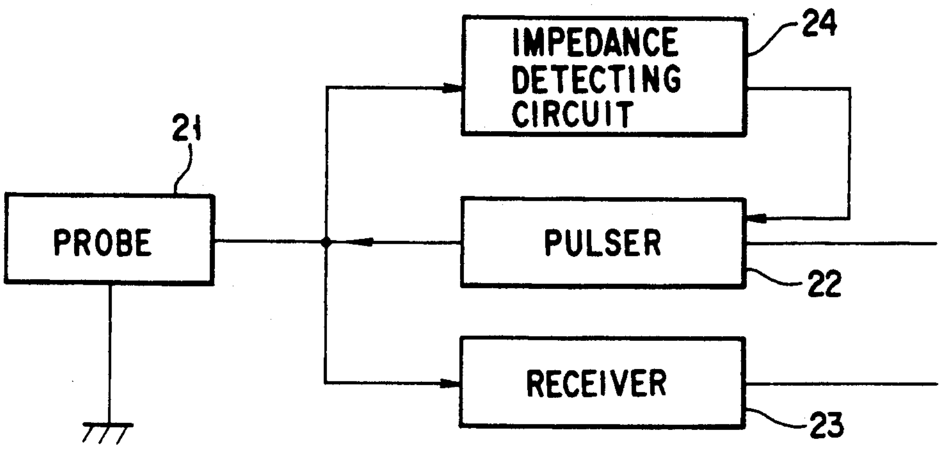
FIG. 3 is a schematic diagram showing an apparatus having a heat control function of an ultrasonic probe according to Example 5 of the present invention.
Figure 4:
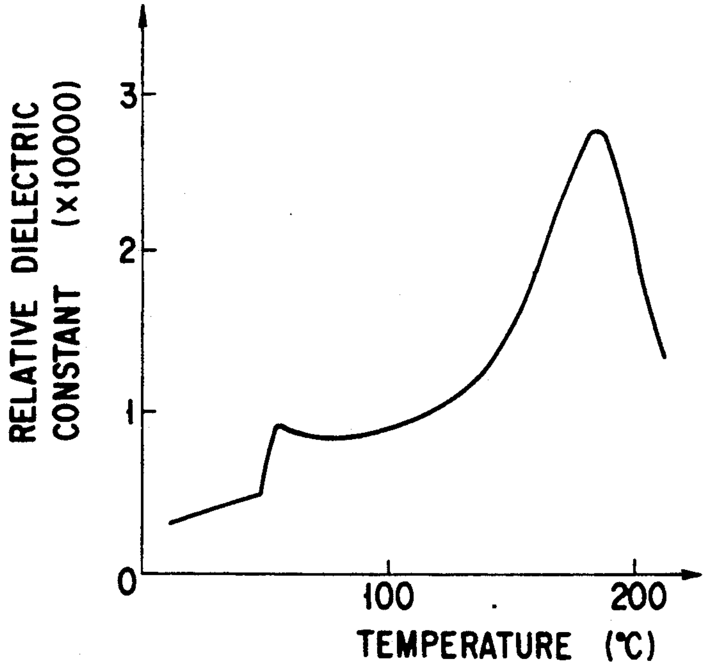
FIG. 4 is a graph showing the relationship between the temperature and the relative dielectric constant of a solid-solution based single crystal of 91PZN-9PT as a piezoelectric member used in the ultrasonic probe of FIG. 3.

FIG. 3 is a schematic diagram showing an apparatus having an ultrasonic probe and a heat control function of the probe. Referring to FIG. 3, reference numeral 21 denotes an array-type ultrasonic probe of a structure similar to that shown in FIG. 1 described above having a piezoelectric member constituted by the 91PZN-9PT solid-solution based single crystal similar to that described in Example 1. In the 91PZN-9PT solid-solution based single crystal, phase transformation from a rhombohedral crystal to a tetragonal crystal occurs at a temperature of 50 to 70° as indicated in FIG. 4 showing the relationship between the temperature and the relative dielectric constant, and the relative dielectric constant of this solid-solution based single crystal is increased along with this phase transformation. More particularly, although the relative dielectric constant of the solid-solution based single crystal is about 2,200 at room temperature, it is increased to 3,500 at 50° C. due to the phase transformation.

A pulser 22 for generating a pulse is connected to the ultrasonic probe 21 via a cable. A receiver 23 is connected to the ultrasonic probe 21 via a cable. An impedance detecting circuit 24 is connected to the ultrasonic probe 21 via a cable. The impedance detecting circuit 24 detects a change in impedance related to the relative dielectric constant of the ultrasonic probe 21. The impedance detecting circuit 24 is connected to the pulser 22, and the pulse (voltage) to be applied by the pulser 22 to the ultrasonic probe 21 is controlled based on the detection result of the impedance detecting circuit 24. For example, the impedance detecting circuit 24 performs control so that when the impedance of the ultrasonic probe 21 becomes ¾ times that obtained when no voltage is applied to the ultrasonic probe 21, the voltage to be applied by the pulser 22 to the ultrasonic probe 21 is set to ½ that obtained when no voltage is applied to the ultrasonic probe 21.

When the ultrasonic probe 21 of the apparatus shown in FIG. 3 is inserted in the body cavity and a voltage is applied by the pulser 22 to the ultrasonic probe 21, the generated ultrasonic waves are mostly radiated on a predetermined portion of the living body and partly absorbed by the acoustic matching layers, the acoustic lens, and the backing member constituting the ultrasonic probe 21 to generate heat. When the ultrasonic probe 21 generates heat in this manner, the relative dielectric constant of the solid-solution based single crystal as the piezoelectric member of the ultrasonic probe 21 is increased, as shown in FIG. 4 described above. The ultrasonic probe 21 is connected to the impedance detecting circuit 24 for detecting the impedance related to the relative dielectric constant. Therefore, when the relative dielectric constant of the piezoelectric member of the ultrasonic probe 21 becomes a predetermined value or more (e.g., 3,500 or more), a signal is output from the impedance detecting circuit 24 to the pulser 22, a voltage ½ that obtained before the signal is output is applied by the pulser 22 to the ultrasonic probe 21, and excessive heat generation of the ultrasonic probe 21 is suppressed.

Figure 5:
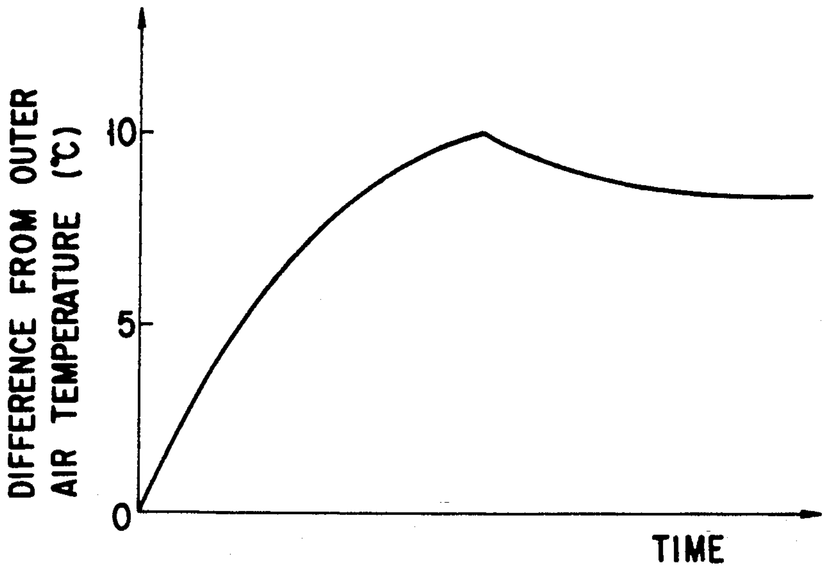
FIG. 5 is a graph showing how the temperature difference between the apparatus shown in FIG. 3 and the outer air change when heat-generation control is performed on the probe.

A thermocouple was actually placed on the surface of the acoustic lens of the ultrasonic probe 21, and heat generation occurring when the ultrasonic probe 21 left in air was measured. The graph of FIG. 5 is a graph representing the change in temperature difference between the ultrasonic probe 21 and the outer air. From FIG. 5 it is apparent that the heat generated by decreasing the drive voltage to ½ was decreased by applying a feedback from the impedance detecting circuit 24 to the pulser 22 when the temperature of the ultrasonic probe 21 rose 10° C. higher than room temperature.

As described above, according to the apparatus of Example 5, the amount of generated heat of the ultrasonic probe 21 can be read by the impedance detecting circuit 24 as an impedance change from a change in relative dielectric constant of the piezoelectric member constituted by the 91PZN-9PT incorporated in the ultrasonic probe 21. Therefore, as the drive voltage to the ultrasonic probe 21 can be controlled based on the impedance change, the body cavity portion of the patient can be prevented from being excessively heated and cause a low-temperature burn. In addition, since the drive voltage can be increased when the ultrasonic probe 21 generates heat at a low temperature, a high-sensitivity signal can be obtained, and the diagnosing performance can be improved. For example, conventionally, when no impedance detecting circuit is provided, the drive voltage must be suppressed to 57 V due to heat generation of the ultrasonic probe. However, in the apparatus of Example 5, the drive voltage can be set to 96 V, which is higher than 57 V, with a low side lobe level of 4.5 dB. As a result, in sensitivity measurement using a phantom having an attenuation of 0.5 dB/MHz.cm, the apparatus of Example 5 capable of increasing the drive voltage to 96 V could increase penetration by about 2 cm when compared to that of the conventional technique wherein the drive current can only be set to 57 V.

Example 6

Figure 6:
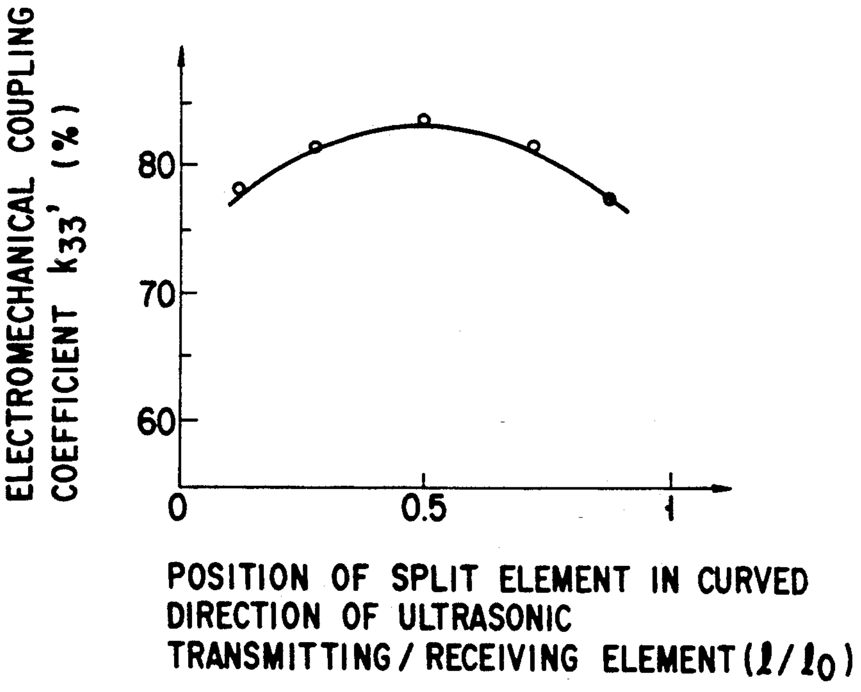
FIG. 6 is a graph showing an electromechanical coupling coefficient of an ultrasonic transmitting/receiving element, which has a curved ultrasonic transmitting/receiving surface in a recessed manner, in the curved direction.

The 91PZN-9PT single crystal obtained by Example 1 was diced at the (001) plane and formed in the recessed manner such that the (001) plane becomes its central portion, thereby forming a single-crystal piece having a predetermined uniform thickness. Ti/Au electrodes were formed on the recessed surface (ultrasonic wave transmitting surface) and the projecting surface of this single-crystal piece by sputtering, an electric field of 1 kV/mm was applied in a silicone oil at a temperature of 150° to 200° C. for 30 minutes, and the single-crystal piece was cooled while applying the electric field. The single-crystal piece, together with its electrodes, was diced into a strip in the curved direction of the single-crystal piece, thereby forming an ultrasonic transmitting/receiving element in which the electrodes were formed on the recessed and projecting surfaces of the curved piezoelectric member. This element was split into 5 pieces in a direction perpendicular to the curved direction of the piezoelectric member, and the electromechanical coupling coefficient ($k_{33}'$) was measured. FIG. 6 shows the obtained results. Note that in FIG. 6, the abscissa represents the position of each split element as $l/l_0$ where $l_0$ is the length of the ultrasonic transmitting/receiving element in the curved direction and l is the length from one end of the element to one end of each split element.

As is apparent from FIG. 6, it is apparent that in an element comprising a piezoelectric member having a recessed ultrasonic wave radiating surface and a central portion with a crystal orientation of the (001) plane, the electromechanical coupling coefficient is large at the central portion and is decreased toward the end portion.

An array-type ultrasonic probe having the same structure as that shown in FIG. 2 was manufactured by using a 91PZN-9PT single-crystal piece which was formed in the recessed manner so as to have the (001) plane as its central portion and a predetermined uniform thickness. More specifically, Ti/Au conductive films were formed on the recessed and projecting surfaces of this single-crystal piece by sputtering. A ground electrode plate 16 was bonded, by using a conductive paste, on the end portion of the conductive film located on the recessed surface of the single-crystal piece in a direction perpendicular to the curved direction of the single-crystal piece. An acoustic matching layer having a predetermined uniform thickness and a recessed curved surface, in the same manner as the single-crystal piece, was formed on the conductive film located on the recessed surface of the single-crystal piece including the ground electrode plate 16. Subsequently, a flexible printed wiring board 17 having a plurality of conductors (cables) was bonded, by using a conductive paste, on the end portion of the conductive film located on the projecting surface of the single-crystal piece in a direction perpendicular to the curved direction of the single-crystal piece, and the resultant structure was bonded on the backing member 12 with an epoxy resin. Then, by using a blade having a thickness of 30 μm, dicing was performed from the acoustic matching layer to the single-crystal piece in a direction parallel to the curved direction of the single-crystal piece at a depth of cut of 1 mm and a pitch of 0.19 mm, thus forming strips. By this dicing, a plurality of separated piezoelectric members 11 each having first and second electrodes 13 and 14, and having a plurality of acoustic matching layers 15 respectively arranged on the corresponding piezoelectric members 11 were formed on the backing member 12, thus manufacturing an array-type ultrasonic probe.

Figure 7:
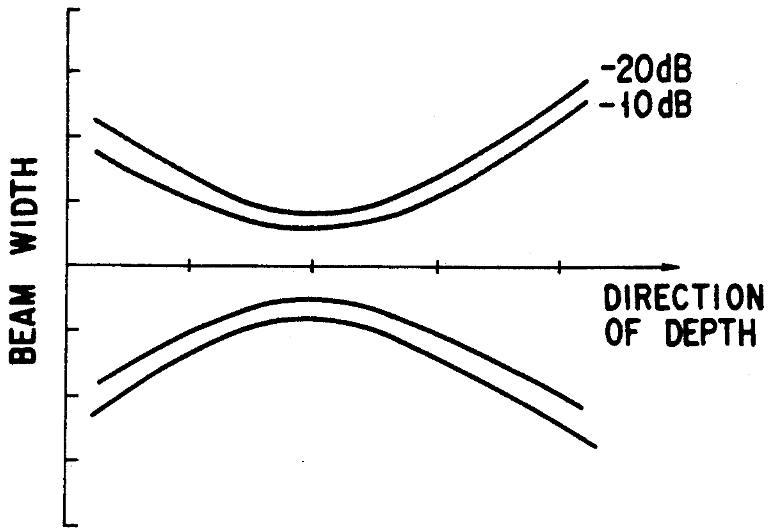
FIG. 7 is a graph showing the result of sound field measurement of an array-type ultrasonic probe according to Example 6 of the present invention.

The sound field of the piezoelectric member was measured by using this ultrasonic probe. FIG. 7 shows the results obtained.

Figure 8:
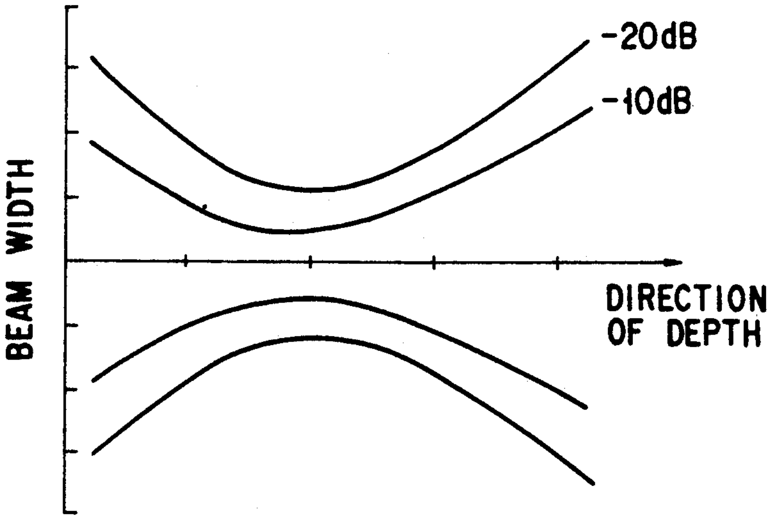
FIG. 8 is a graph showing the result of sound field measurement of an array-type ultrasonic probe having a plate-like piezoelectric member.

For the purpose of comparison, an array-type ultrasonic probe was manufactured which had a structure similar to that shown in FIG. 2 described above except that the piezoelectric member constituted by the 91PZN-9PT single crystal was formed as a flat plate and an acoustic lens was formed on the acoustic matching layers. The sound field of this ultrasonic probe was measured in the same manner. FIG. 8 shows the results obtained.

As is apparent from FIGS. 7 and 8, the ultrasonic probe of Example 6 exhibited a remarkable difference especially in a beam width of −20 dB as compared to the ultrasonic probe having a flat piezoelectric member. It was confirmed that since the ultrasonic probe of Example 6 had a suppressed side lobe level, it had a fine beam. Furthermore, it was confirmed that the S/N ratio of the signal of the ultrasonic probe of Example 6 was increased by 5 dB as compared to that of the ultrasonic probe using an acoustic lens.

In Example 6, bonding of the ground electrode plate 16 and the conductive film, and bonding of the flexible printed wiring board 17 and the conductive film may be performed by welding or resistance welding, in addition to the method using the conductive paste.

Example 7

The [001]-axis orientation of the 91PZN-9PT single crystal obtained in Example 1 was obtained by using a Laue camera, and the single crystal was diced by a cutter in a direction perpendicular to this axis. Subsequently, Ti/Au electrodes were formed on the surfaces of the (001) plane of the diced single-crystal piece by sputtering. An electric field of 1 kV/mm was applied to the single-crystal piece in a silicone oil of 150° to 200° C. for 30 minutes, and the single-crystal piece was cooled while applying the electric field. This single-crystal piece, together with its electrodes, was cut into elements each having a regular hexagonal shape, and the capacitance, the resonance frequency, and the anti-resonance frequency of the regular hexagonal element were measured. As a result, it was confirmed that the relative dielectric constant was 2,200, the sound velocity was 3,250 m/s, and the electromechanical coupling coefficient $K_t$ was 70 to 75%.

Figure 9:
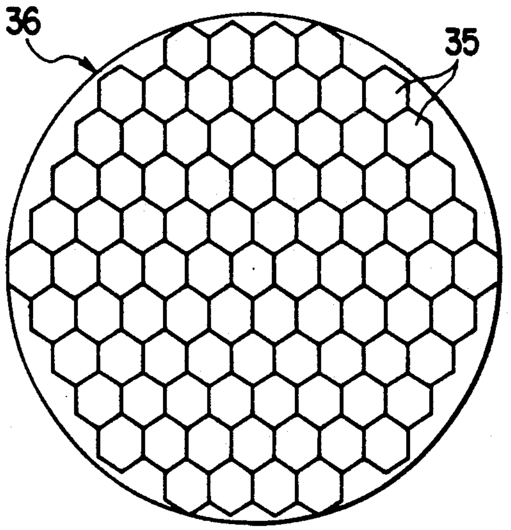
FIG. 9 is a plan view showing a transmitter of Example 7 of the present invention.
Figure 10:
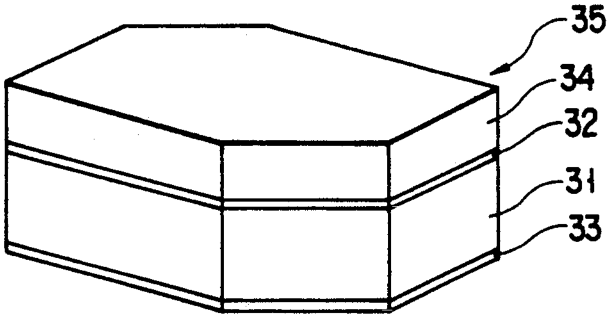
FIG. 10 is a perspective view showing an ultrasonic generating element incorporated in the wave transmitter of FIG. 9.

Furthermore, a transmitter 36 having a plurality of ultrasonic generating elements 35 shown in FIG. 9 was manufactured by using the 91PZN-9PT single crystal. More specifically, as shown in FIG. 10, a piezoelectric member 31 having a thickness set to have a resonance frequency of 500 kHz was cut from this single crystal, Ti/Au electrodes 32 and 33 were formed on the surfaces of the (001) plane of this piezoelectric member 31, and an acoustic matching layer 34 was formed on the upper electrode 32, thus fabricating each ultrasonic generating element 35. The plurality of ultrasonic generating elements 35 were closely arranged to form a substantial sphere having a diameter of 330 mm and a radius of 260 mm, thus manufacturing the transmitter 36 shown in FIG. 9 described above.

In this transmitter 36, the thickness of the piezoelectric member 31 incorporated in each ultrasonic generating element 35 could be set to about 3.2 mm, which was smaller than the thickness (4 mm) of the conventional piezoelectric member constituted by the PZT-based ceramic. As a result, each ultrasonic generating element 35 could apply, from its electrodes 32 and 33, an electric field larger than that of the ultrasonic generating element having the conventional piezoelectric member constituted by the PZT-based ceramic by 25%. Also, the weight of each ultrasonic generating element 35 was decreased by 20% that of the conventional ultrasonic generating element, thus decreasing the overall weight of the apparatus.

Figure 11A:
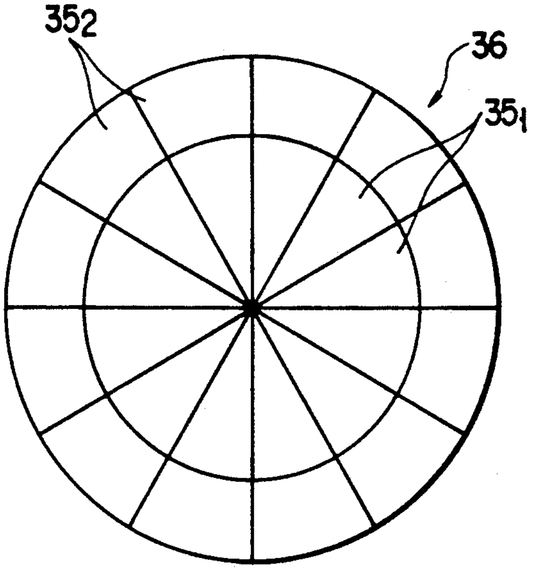
FIG. 11A is a front view showing another arrangement of the transmitter.
Figure 11B:
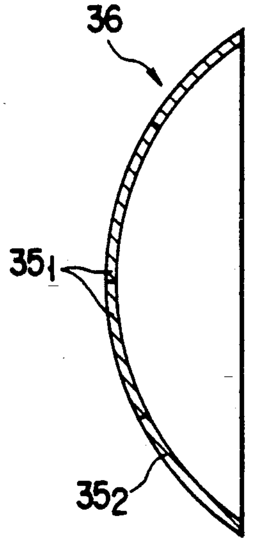
FIG. 11B is a sectional view of the transmitter of FIG. 11A.

In Example 7, regular hexagonal ultrasonic generating elements were closely arranged to form a transmitter. However, the present invention is not limited to this. For example, as shown in FIGS. 11A and 11B, fan-shaped ultrasonic generating elements 35$_1$ and trapezoidal ultrasonic generating elements 35$_2$ each having curved opposite sides of different lengths may be closely spherically arranged, thus forming a transmitter 36.

Examples 8-12, Reference Examples 4 and 5

PbO, ZnO, $Nb_2O_5$, and $TiO_2$ each having a high chemical purity were used as the starting materials. The starting materials were purity-corrected, weighed in predetermined amounts, and the same amount of PbO was added to the resultant powder as the flux. Alcohol was added to the resultant powder and mixed for 1 hour in a ball mill containing $ZrO_2$ balls. Alcohol was removed from the obtained mixture. The mixture was sufficiently pulverized by a Raika machine, was placed in a rubber mold container, and was rubber-pressed at a pressure of 2 t/cm$^2$. 1,000 g of a solid material removed from the rubber mold were placed in a platinum container having a diameter of 50 mm and a volume of 250 cc and sealed with a platinum lid, and the container was placed at the center of an electric furnace. The temperature was increased up to 1,000° to 1,280° C. within 5 hours and was then slowly decreased down to 700° to 900° C. at a rate of 0.5° C./hr to 5° C./hr. Then, nitric acid having a concentration of 30% was added in the platinum container, the content in the container was boiled for 24 hours to melt the flux portion, and the fabricated solid-solution based single crystal was removed from the container. The single crystal obtained in accordance with this flux method had a non-fixed shape and a size of about 20 mm square. When part of the single crystal was pulverized and subjected to X-ray diffraction, it was confirmed to have a good crystal structure. When the pulverized powder was subjected to chemical analysis in accordance with ICP, it was confirmed to have a composition of 91PZN-9PT in which zinc niobate (PZN) and lead titanate (PT) had a molar ratio of 91:9.

The [001]-axis orientation of the single crystal was obtained by using a Laue camera, and the single crystal was cut by a cutter in a direction perpendicular to this axis to form 7 single-crystal pieces. The two surfaces of each single-crystal piece, i.e., the ultrasonic transmitting/receiving surface and a surface opposite to the transmitting/receiving surface were abraded with #400 to #8,000 abrasive grains made of alumina or silicon carbide, or a paste containing a 1-$\mu$m diameter cerium oxide powder. The surface roughness of each single-crystal piece after abrasion was measured by using a contact type surface roughness meter at ten locations with an interval of 1 mm. The following Table 3 shows the maximum surface roughness and the average surface roughness obtained by this measurement. Subsequently, Ni/Au electrodes were formed on the two abraded surfaces of each single-crystal piece by sputtering. An electric field of 0.5 to 1 kV/mm was applied to the single-crystal piece in a silicone oil of 150° to 200° C. for 15 minutes, and the single-crystal piece was cooled down to 40° C. while applying the electric field. Each single-crystal piece, together with its electrodes, was diced into a strip and the capacitance, the resonance frequency, and the anti-resonance frequency of the strip were measured. As a result, it was confirmed that the relative dielectric constant was 3,000 and the sound velocity was 2,850 m/s. Also, the electromechanical coupling coefficient $k_{33}'$ was as shown in Table 3 below.

TABLE 3

| | Abrasive Grain # | Maximum Surface Roughness Rmax ($\mu$m) | Average Surface Roughness Ra. ($\mu$m) | Coupling Coefficient $K_{33}$ (%) |
|---|---|---|---|---|
| Reference Example 4 | 400 | 4.9 | 0.87 | 77.5 |
| Reference Example 5 | 800 | 4.2 | 0.52 | 79.4 |
| Example 8 | 1,500 | 3.6 | 0.38 | 82.3 |
| Example 9 | 2,500 | 3.0 | 0.30 | 82.9 |
| Example 10 | 4,000 | 2.2 | 0.24 | 83.7 |
| Example 11 | 8,000 | 1.9 | 0.18 | 84.1 |
| Example 12 | $CeO_2$ paste | 0.8 | 0.08 | 84.8 |

Furthermore, this single crystal was diced so as to have a thickness of 300 $\mu$m in the direction of vibration, and abraded with an abrasive grain or a paste containing a cerium oxide powder, in the manner as described above, thereby forming single-crystal pieces. Using seven single-crystal pieces fabricated in this manner, array-type ultrasonic probes each having 96 elements and having the same structure as that shown in FIG. 1 were manufactured following substantially the same procedures as that of Example 1. Note that dicing with a blade having a width of 30 $\mu$m was performed at a depth of cut of 1 mm and a pitch of 0.13 mm, and each of the obtained 96 piezoelectric members had a width of about 80 $\mu$m.

The reflected echo of each obtained ultrasonic probe was measured in accordance with the pulse echo method. As a result, all the ultrasonic transmitting-/receiving elements radiated echoes each having a center frequency of about 3.75 MHz.

Each of the obtained array-type ultrasonic probes was subjected to the actual operation tests of 1,000 hours and 3,000 hours each with a rectangular double pulse having a repetition frequency of 5 kHz, a voltage of 100 V, a duty ratio of 1:1, and a pulse width of 0.2 $\mu$s. The peak value of the reflected echo was measured. The number of defective ones of the 96 elements incorporated in each probe was checked with a definition that an element whose peak value was degraded by 30 or more the value obtained before the actual operation tests was a defective element. The following Table 4 shows the results.

TABLE 4

| | Number of Defective Elements After Actual Operation Test of 1,000 hours | Number of Defective Elements After Actual Operation Test of 3,000 hours |
|---|---|---|
| Example 8 | 0/96 | 2/96 |
| Example 9 | 0/96 | 0/96 |
| Example 10 | 0/96 | 0/96 |
| Example 11 | 0/96 | 0/96 |
| Example 12 | 0/96 | 0/96 |
| Reference Example 4 | 47/96 | 55/96 |
| Reference | 21/96 | 29/96 |

TABLE 4-continued

| | Number of Defective Elements After Actual Operation Test of 1,000 hours | Number of Defective Elements After Actual Operation Test of 3,000 hours |
|---|---|---|
| Example 5 | | |

As is apparent from Tables 3 and 4, the ultrasonic probes of Examples 8 to 12 each having a piezoelectric member having an ultrasonic transmitting/receiving surface and a surface opposite to the transmitting-/receiving surface with an average surface roughness of 0.4 μm or less and a maximum surface roughness of 4 μm or less not only have a large electromechanical coupling coefficient $k_{33}'$ but also high reliability over a long period of time.

Ultrasonic probes having the same structures as that shown in FIG. 1 were manufactured by using piezoelectric members diced from single crystals obtained by changing the amount of lead titanate in the solid-solution based single crystal of zinc lead niobate-lead titanate in the range of 5 to 20 mol % or from single crystals also containing magnesium or zirconium. These ultrasonic probes had almost the same effects on the long-term reliability resulted from the surface roughness.

As has been described above, according to the present invention, low-frequency driving can be achieved and the thickness of the piezoelectric member in the direction of vibration can be decreased, so that an ultrasonic probe which can be easily matched with a transmitting/receiving circuit, which has an ultrasonic transmitting/receiving element capable of increasing its sensitivity, and which is effective in, e.g., a medical diagnosing apparatus, can be provided.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic probe comprising an ultrasonic transmitting/receiving element having a piezoelectric member consisting of a solid-solution based single crystal of zinc lead niobate-lead titanate, and a pair of electrodes formed on an ultrasonic transmitting/receiving flat surface of said piezoelectric member and a surface opposite to said transmitting/receiving flat surface, respectively.

2. A probe according to claim 1, wherein said solid-solution based single crystal of zinc lead niobate-lead titanate has a composition represented by a formula:

$$Pb_A[(Zn_{1/3}Nb_{2/3})_{1-x}Ti_x]_BO_3$$

wherein x is defined by the relationship $0.05 \leqq x \leqq 0.20$.

3. A probe according to claim 1, wherein said solid-solution based single crystal of zinc lead niobate-lead titanate has a composition represented by a formula:

$$Pb_A[(Zn_{1/3}Nb_{2/3})_{1-x}Ti_x]_BO_3$$

wherein x is defined by the relationship: $0.05 \leqq x \leqq 0.20$, and a stoichiometric ratio A/B is defined by the relationship: $0.98 \leqq A/B < 1.00$.

4. A probe according to claim 1, wherein x in the formula is 0.06 to 0.12.

5. A probe according to claim 1, wherein said ultrasonic transmitting/receiving surface and said flat surface opposite to said transmitting/receiving surface of said piezoelectric member have an average surface roughness of not more than 0.4 μm and a maximum surface roughness of not more than 4 μm.

6. A probe according to claim 1, wherein said ultrasonic transmitting/receiving surface of said piezoelectric member is on a (001) plane.

7. A probe according to claim 1, wherein said piezoelectric member has a thickness of 200 to 400 μm in a direction of vibration.

8. A probe according to claim 1, wherein said ultrasonic transmitting/receiving element comprises a plurality of ultrasonic transmitting/receiving elements.

9. An array-type ultrasonic probe in which a plurality of ultrasonic transmitting/receiving elements having a piezoelectric member consisting of a single crystal and a pair of electrodes formed on an ultrasonic transmitting/receiving surface of said piezoelectric member and a surface opposite to said transmitting/receiving surface are aligned, wherein said piezoelectric member has a predetermined uniform thickness, and has said ultrasonic transmitting/receiving surface curved in a recessed manner and extending at right angles to a direction along which said elements are arranged, and said recessed ultrasonic transmitting/receiving surface has an electromechanical coupling coefficient which is maximum in the central portion and gradually decreased from the control portion toward the end portions.

10. A probe according to claim 9, wherein said piezoelectric member consists of a solid-solution based single crystal of zinc lead niobate-lead titanate.

11. A probe according to claim 10, wherein said solid-solution based single crystal of zinc lead niobate-lead titanate has a composition represented by a formula:

$$Pb_A[(Zn_{1/3}Nb_{2/3})_{1-x}Ti_x]_BO_3$$

wherein x is defined by the relationship $0.05 \leqq x \leqq 0.20$.

12. A probe according to claim 10, wherein said solid-solution based single crystal of zinc lead niobate-lead titanate has a composition represented by a formula:

$$Pb_A[(Zn_{1/3}Nb_{2/3})_{1-x}Ti_x]_BO_3$$

wherein x is defined by the relationship: $0.05 \leqq x \leqq 0.20$, and a stoichiometric ratio A/B is defined by the relationship: $0.98 \leqq A/B < 1.00$.

13. A probe according to claim 12, wherein x in the formula is 0.06 to 0.12.

14. A probe according to claim 10, wherein said recessed ultrasonic transmitting/receiving surface and a projecting surface opposite to said recessed transmitting/receiving surface of said piezoelectric member have an average surface roughness of not more than 0.4 μm and a maximum surface roughness of not more than 4 μm.

15. A probe according to claim 10, wherein the central portion of said recessed ultrasonic transmitting-/receiving surface is on a (001) plane.

16. A probe according to claim 10, wherein said piezoelectric member has a thickness of 200 to 400 $\mu m$ in a direction of vibration.

17. An ultrasonic transducer comprising a piezoelectric member having two flat surfaces and consisting of a solid-solution based single crystal of zinc lead niobate-lead titanate represented by a formula:

$$Pb_A[(Zn_{1/3}Nb_{2/3})_{1-x}Ti_x]_BO_3$$

wherein x is defined by the relationship: $\leqq 0.20$, and a stoichiometric ratio A/B is defined by the relationship: $0.98 \leqq A/B \leqq 1$ and a pair of electrodes is formed on the two surfaces of said piezoelectric member.

18. An ultrasonic transducer according to claim 17, wherein said two flat surfaces of said piezoelectric member have an average surface roughness of not more than 0.4 $\mu m$ and a maximum surface roughness of not more than 4 $\mu m$.

19. An ultrasonic transducer according to claim 17, wherein at least one flat surface of said piezoelectric member is on a (001) plane.

* * * * *